United States Patent
Taube et al.

(10) Patent No.: US 9,867,831 B2
(45) Date of Patent: Jan. 16, 2018

(54) COMBINATION TREATMENT OF ACUTE MYELOID LEUKEMIA AND MYELODYSPLASTIC SYNDROME

(71) Applicant: Boehringer Ingelheim International GmbH, Ingelheim am Rhein (DE)

(72) Inventors: Tillmann Taube, Biberach an der Riss (DE); Dorothea Rudolph, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/859,422

(22) Filed: Sep. 21, 2015

(65) Prior Publication Data
US 2016/0095863 A1   Apr. 7, 2016

(30) Foreign Application Priority Data

Oct. 1, 2014   (EP) .................................... 14187331

(51) Int. Cl.
*A61K 31/5377* (2006.01)
*A61K 31/519* (2006.01)

(52) U.S. Cl.
CPC ........ *A61K 31/5377* (2013.01); *A61K 31/519* (2013.01)

(58) Field of Classification Search
CPC .......................... A61K 31/5377; A61K 31/519
See application file for complete search history.

(56) References Cited

U.S. PATENT DOCUMENTS

| | | |
|---|---|---|
| 4,870,175 A | 9/1989 | Suzuki et al. |
| 4,957,922 A | 9/1990 | Lammens et al. |
| 5,043,270 A | 8/1991 | Abrams et al. |
| 5,167,949 A | 12/1992 | Ferrand et al. |
| 5,198,547 A | 3/1993 | Bailey et al. |
| 5,424,311 A | 6/1995 | Billhardt-Troughton et al. |
| 5,698,556 A | 12/1997 | Chan |
| 6,096,924 A | 8/2000 | Studer et al. |
| 6,156,766 A | 12/2000 | Arita et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 6,875,868 B2 | 4/2005 | Bonnert et al. |
| 6,960,589 B2 | 11/2005 | Cowart et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,557,189 B2 * | 7/2009 | Hoffee .............. C07K 16/2803 424/130.1 |
| 7,625,899 B2 | 12/2009 | Hoffmann et al. |
| 7,626,019 B2 | 12/2009 | Duran et al. |
| 7,629,460 B2 | 12/2009 | Grauert et al. |
| 7,638,627 B2 | 12/2009 | Kankan et al. |
| 7,700,769 B2 | 4/2010 | Grauert et al. |
| 7,723,517 B2 | 5/2010 | Grauert et al. |
| 7,728,134 B2 | 6/2010 | Linz et al. |
| 7,750,152 B2 | 7/2010 | Hoffman et al. |
| 7,759,347 B2 | 7/2010 | Hoffmann |
| 7,759,485 B2 | 7/2010 | Linz et al. |
| 7,807,831 B2 | 10/2010 | Grauert et al. |
| 7,816,530 B2 | 10/2010 | Grauert |
| 8,003,786 B2 | 8/2011 | Hoffmann et al. |
| 8,034,816 B2 | 10/2011 | Linz et al. |
| 8,058,270 B2 | 11/2011 | Munzert et al. |
| 8,138,341 B2 | 3/2012 | Linz et al. |
| 8,138,373 B2 | 3/2012 | Linz et al. |
| 8,143,247 B2 | 3/2012 | Munzert et al. |
| 8,188,086 B2 | 5/2012 | Linz et al. |
| 8,193,188 B2 | 6/2012 | Hoffmann et al. |
| 8,202,867 B2 | 6/2012 | Linz et al. |
| 8,329,695 B2 | 12/2012 | Linz et al. |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2003/0162790 A1 | 8/2003 | Cowart et al. |
| 2004/0024205 A1 | 2/2004 | Borredon et al. |
| 2004/0029885 A1 | 2/2004 | Bauer et al. |
| 2004/0127504 A1 | 7/2004 | Cowart et al. |
| 2004/0147524 A1 | 7/2004 | Bauer et al. |

(Continued)

FOREIGN PATENT DOCUMENTS

| CA | 2458699 A1 | 3/2003 |
|---|---|---|
| CA | 2517020 A1 | 9/2004 |

(Continued)

OTHER PUBLICATIONS

Verschuren, E.W. et al., "The cell cycle and how it is steered by Kaposi's sarcoma-associated herpesvirus cyclin". Journal of General Virology, 2004, 85, pp. 1347-1361.
Vippagunta, S. R. et al., "Crystalline solids". Advanced Drug Delivery Reviews, 48, 2001, pp. 3-26.
Visiting Nurse Association of America. www.vnaa.org/gen/Germ_Protection_Center_Cold_and_Flu_Resources,html, 2009.
Voskoglou-Nomikos, T. et al., "Clinical predictive value of the in vitro cell line, human xenograft, and mouse allograft preclinical cancer models". Clinical Cancer Research vol. 9, 2003, pp. 4227-4239.
Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

(Continued)

*Primary Examiner* — Sahar Javanmard
(74) *Attorney, Agent, or Firm* — Marc Began; Usha R. Patel

(57) ABSTRACT

The present invention relates to the use of Volasertib or a salt thereof or the hydrate thereof in combination with Quizartinib or a salt thereof or the hydrate thereof for treating patients suffering from acute myeloid leukemia (AML) or myelodysplastic syndrome (MDS).

15 Claims, 1 Drawing Sheet

(56) References Cited

U.S. PATENT DOCUMENTS

| | | |
|---|---|---|
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0063735 A1 | 3/2006 | Redkar et al. |
| 2006/0074088 A1 | 4/2006 | Munzert et al. |
| 2006/0079503 A1 | 4/2006 | Schwede et al. |
| 2007/0043055 A1 | 2/2007 | Maier et al. |
| 2007/0117776 A1 | 5/2007 | Lyons |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0029990 A1 | 1/2009 | Maier et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2009/0306101 A1 | 12/2009 | Solca et al. |
| 2010/0029642 A1 | 2/2010 | Hoffmann et al. |
| 2010/0179134 A1 | 7/2010 | Singh et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |
| 2011/0046176 A1 | 2/2011 | Moore, II et al. |
| 2012/0107312 A1 | 5/2012 | Munzert et al. |
| 2012/0214995 A1 | 8/2012 | Linz et al. |
| 2012/0238754 A1 | 9/2012 | Schnaubelt et al. |
| 2012/0295864 A1 | 11/2012 | Taube et al. |
| 2012/0296091 A1 | 11/2012 | Sieger et al. |
| 2012/0329803 A1 | 12/2012 | Linz et al. |
| 2013/0012465 A1 | 1/2013 | Haslinger et al. |

FOREIGN PATENT DOCUMENTS

| | | |
|---|---|---|
| CA | 2517010 A1 | 11/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |
| ES | 2287583 | 12/2007 |
| JP | 2009169737 A | 6/1997 |
| RU | 2002125451 A | 1/2004 |
| WO | 9608537 A1 | 3/1996 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 03020722 A1 | 3/2003 |
| WO | 03093249 A1 | 11/2003 |
| WO | 2004014899 A1 | 2/2004 |
| WO | 2004024728 A2 | 3/2004 |
| WO | 2004076454 A1 | 9/2004 |
| WO | 2004093848 A2 | 11/2004 |
| WO | 2005067935 A1 | 7/2005 |
| WO | 2006005510 A1 | 1/2006 |
| WO | 2006018182 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2006021379 A1 | 3/2006 |
| WO | 2006021547 A1 | 3/2006 |
| WO | 2007014838 A1 | 2/2007 |
| WO | 2007054551 A1 | 5/2007 |
| WO | 2007090844 A1 | 8/2007 |
| WO | 2009019205 A1 | 2/2009 |
| WO | 2009112524 A1 | 9/2009 |
| WO | 2010111172 A1 | 9/2010 |
| WO | 2011101369 A1 | 8/2011 |
| WO | 2012049153 A1 | 4/2012 |
| WO | 2012072505 A1 | 6/2012 |
| WO | 2012156283 A1 | 11/2012 |
| WO | 2012156380 A1 | 11/2012 |

OTHER PUBLICATIONS

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.

Webster's Comprehensive Dictionary, 1996, pp. 1013-1014.

Wikipedia. "Melting Point", Jan. 17, 2007. http://en.wikipedia.org/wiki/Melting_point.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

X-ray Diffraction—Factors that affect d's and I's. [Downloaded from the internet Mar. 9, 2011, URL: http://www.gly.uga.edu/Schroeder/geol6550/XRD.html].

Xu, W-J., "Efficient Inhibition of Human Colorectal Carcinoma Growth by RNA Interference Targeting Polo-Like Kinase 1 in Vitro and in Vivo." Cancer Biotherapy and Radiopharmaceuticals, 2011, vol. 26, No. 4, pp. 427-436.

Lin, C-C et al., "A phase I study of two dosing schedules of volasertib (BI 6727), an intravenous polo-like kinase inhibitor, in patients with advanced solid malignancies." British Journal of Cancer, 2014, pp. 1-7.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

Mashkovkii, M.D., "Medicaments". Moscow, Novaja Volna, 2001, vol. 1, p. 11.

Mashkovskii, M.D. "Drugs", Handbook for Doctors, 1993, Part I, Ch.1, p. 8.

Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.

Mayer, SF, et al., "Enzyme-initiated domino (cascase) reactions". Chem. Soc. Rev, 2001, p. 332-339.

Medema et al.; Polo-like Kinase 1 Inhibitors and Their Potential Role in Anticancer Therapy, with a Focus on NSCL; Clinical Cancer Research; 2011; vol. 17; No. 20; pp. 6459-6466.

(56) References Cited

OTHER PUBLICATIONS

MedlinePlus: Bacterial Infections. www.nim.nih.gov/medlineplus/print/bacterialinfections.htm, date last updated Mar. 25, 2009.
MedlinePlus: Viral Infections. www.nim.nih.gov/medlineplus/print/viralinfections.htm, date last updated Feb. 11, 2009.
Merck Manual of Medical Information—Home Edition, Section 17. "Parasitic Infections". Chapter 184, 2003.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Mito, K., et al., "Expression of polo-like kinase (PLK1) in non-Hodgkin's lymphomas". NCBI, PubMed, 2005, Leuk. Lymphoma, 46(2), pp. 251-231.
Morris, K.R. et al., "An integrated approach to the selection of optimal salt form for a new drug candidate", International Journal of Pharmaceutics, 105, 1994, 209-217.
Mross, K. et al., A randomised phase II trial of the polo-like kinase inhibitor BI 2536 in chemo-naieve patients with unresectable exocrine adenocarcinoma of the pancreas—a study within the Central European Society Anticancer Drug research (CESAR) collaaborative work. British Journal of Cancer, 2012, p. 1-7.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
Neau, S. H., Pharmaceutical Salts, CRC Press, 2008, Ch 17, p. 417-435.
Neidle, S. ed., "Cancer Drug Design and Discovery", Elsevier/Academic Press, 2008, p. 427-431.
Norman, P. "PDE4 inhibitors". Ashley Publications Ltd., Expert Opinions Ther. Patents, 1999, pp. 1101-1118.
Office Action dated Dec. 10, 2003 for U.S. Appl. No. 10/226,710, filed Aug. 23, 2002. Inventor: Eckhart Bauer.
Office Action dated Apr. 28, 2004 for U.S. Appl. No. 10/374,876, filed Feb. 26, 2003 Inventor: Matthias Hoffmann.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983 (available in Spanish).
Phys. Org. "New way of inhibiting cell cycle shows promise." Oct. 22, 2008, pp. 1-2. http://phys.org/news143890171.html.
Roberts, Jr., T. G. et al. "Trends in the Risks and Benefits to Patients with Cancer Participating in Phase 1 Clinical Trials". JAMA, Nov. 3, 2004, vol. 292, No. 17, p. 2130-2140.
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.
Rudolph et al., "BI 6727, a Polo-like kinase inhibitor with improved pharmacokinetic profile and broad antitumor activity." Clinical Cancer Research, 2009, vol. 15, No. 9, Abstract only.
Rudolph, D. et al., "430 Poster Characterization of BI 6727, a novel Polo-like kinase inhibitor with a distinct pharmacokinetic profile and efficacy in a model of taxane-resistant colon cancer". European Journal of Cancer. Supplement, Pergamon, Oxford, GB, vol. 6, No. 12, Oct. 1, 2008, p. 135. [retrieved on Oct. 1, 2008].
Rudolph, D. et al., "BI 6727, a Polo-like Kinase Inhibitor with Improved Pharmacokinetic Profile and Broad Antitumor Activity." Clinical Cancer Research, 2009, vol. 15, No. 9, pp. 3094-3102 (Updated Full Text).
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Rylander, P.N., "Hydrogenation Methods". 1985, Chapters 1, 2.
Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.
Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.
Schoffski et al., Polo-Like Kinase (PLK) Inhibitors in Preclinical and Early Clinical Development in Oncology, The Oncologist, 2009, 14:559-570.
Schoffski, P. et al., "A phase I, dose-escalation study of the novel Polo-like kinase inhibitor volasertib (BI 6727) in patients with advanced solid tumors." European Journal of Cancer, 2012, vol. 48, pp. 179-186.
Schoffski, P., "Polo-like kinase (PLK) inhibitors in preclinical and early clinical development in oncology", The Oncologist, vol. 14, 2009, pp. 559-570.
Schoffski, P., et al., "A phase I single dose escalation study of the novel polo-like kinase 1 inhibitor BI 6727 in patients with advanced solid tumours", EJC Supplement, vol. 6. No. 12, Oct. 2008, p. 14-15.
Science, vol. 310, Oct. 21, 2005, p. 409, Chemistry: One After Another.
Seetharam, M. et al., "Treatment of higher risk myelodysplastic syndrome patients unresponsive to hypomethylating agents with ON 01910.Na." Leukemia Research, 2012, vol. 36, pp. 98-103.
Serajuddin, Abu T.M., "Salt formation to improve durg solubility", Advanced Drug Delivery Reviews, 59, 2007, 603-616.
Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.
Souillac, P. et al., "Characterization of delivery systems, differential scanning calorimetry". (In Encyclopedia of Controlled Drug Delivery), 1999, John Wiley & Sons, pp. 212-227.
Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.
Takai, N. et al., "Polo-like kinases (PLKs) and cancer". Oncogene , 2005, 24, pp. 287-291.
Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.
Turner, S., "The Design of Organic Syntheses". Elsevier, 1976, pp. 10 and 149.
Turner, W.W.et al., "Recent advances in the medicinal chemistry of antifungal agents". Current Pharmacutical Design, 1996, 2, pp. 209-224.
"Salt Forms of Drug Absorption", Swarbrick, et al. editors, Encyclopedia of Pharm. Tech. 13 Marcel Dekker, NY, 1996, 453-499.
Abstract in English for JP09169737, Date of Publication: Jun. 30, 1997, Applicant Tosoh Corp, Inventor: K. Hiroyuki, Title: Production of N-Methylimidazoles. Date filed: Dec. 21, 1995.
ACPS Meeting, Background Information. "Scientific considerations of plymorphism in pharmaceutical solids: abbreviated new drug applications". Oct. 2002.
Ahlenius, T. List of cardiovascular disorder/diseases. Ahlenius, Karolinska Institutet. Stockholm, Sweden. Cardiovascular Diseases, p. 1-34, Apr. 2007.
Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.
Arnold, K. "Collaboration to play key role in NCI's future, director says". Journal of the National Cancer Institute, Jun. 5, 2002, pp. 790-792, vol. 94, No. 11.
Awada, A. et al., "Phase I trial of volasertib, a Polo-like kinase inhibitor, plus platinum agents in solid tumors: safety, pharmacokinetics and activity." Invest New Drugs, 2015, vol. 33, No. 3, pp. 611-620.
Badawy, S. I. et al., "Sale Selection for Phamaceutical Compounds", Preformulation in Solid Dosage Form Develolpment, Infoa Healthcare 2008, Chapter 2.3, 63-80.
Bastin, R. J. et al., "Salt Selection and Optimisation Procedures for Pharmaceutical New Chemical Entities", Organic Process Research and Development, 2000, 4,427-435.

(56) References Cited

OTHER PUBLICATIONS

BBC News/Health, Killer Breast Cancern Therapy Hope, www.newsvote.bbc/co./uk, Published Jan. 21, 2006.
Benetatos, L. et al., "Polo-like kinase 2 (SNK/PLK2) is a novel epigenetically regulated gene in acute myeloid leukemia and myelodysplastic syndromes: genetic and epigenetic interactions." Annals of Hematology, 2011, vol. 90, No. 9, pp. 1037-1045.
Bennett, J.C., et al., "Textbook of Medicine", Part XIV, Oncology, 1997.
Berg, T. et al., "Polo-like kinases in AML." Expert Opinion on Investigational Drugs, 2012, vol. 21, No. 8, pp. 1069-1074.
Beshore, D.C.et al., "Preparation of Substituted Piperazinones via Tandem Reductive Amination-N.N-Acyl Transfer)-Cyclization". Organic Letters, 2002, vol. 4, No. 7, p. 1201-1204.
Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.
Boulikas, T. et al., "Recent clinical trials using cisplatin, carboplatin and their combination chemotherapy drugs (Review)." Oncology Reports, 2004, vol. 11, pp. 559-595.
Bug, G. et al., "Phase I/II Study of BI 6727 (volasertib), An Intravenous Polo-Like Kinase-1 (Plk1) Inhibitor, in Patients with Acute Myeloid Leukemia (AML): Results of the Dose Finding for BI 6727 in Combination with Low-Dose Cytarabine." Blood, 2010, vol. 116, pp. 1-2.
Cancer Drug Design and Discovery, Stephen Neidle, Ed. (Elsevier/Academic Press, 2006), p. 427-431.
Chen, J.X. et al., "Parallel differentiated recognition of ketones and acetals". Angewandte Chemie Int. Ed, vol. 37, Issue 1/2, p. 91-93, 1998.
Christoph, D. et al., "Polo-like kinase 1 inhibitors in mono-and combination therapies: a new strategy for treating malignancies." Expert Review of Anticancer Therapy, 2011, vol. 11, No. 7, pp. 1115-1130.
Clinical Trials: NCT01348347. BI6727 (Volasertib) Monotherapy Phase I Trial in Japanese Patients with Advanced Soliid Tumours. Apr. 29, 2011 [Retrieved from the Internet: URL: http://www.clinicaltrials.gov./ct2/show/NCT01348347?term=volasertib &rank=1] retrieved Jul. 16, 2012.
Dipolar aprotic solvent. Exhibit A, IUPAC Compendium of Chemical Terminology, 2nd Edition, 1997.
Doerwald, F.Z. Book Wiley-VCH Verlag GmbH & Co. KGaA, "Side reactions in organice synthesis: A Guide to Successful Synthesis Design". 2005.
Dyson, G, et al. "The Chemistry of Synthetic Drugs". 1964, p. 12-19.
Ellis, P.M. et al., "A Phase I Open-Label Dose-Escalation Study of Intravenous BI 2536 Together with Pemetrexed in Previously Treated Patients with Non-Small-Cell Lung Cancer" Clinical Lung Cancer, 2012, p. 1-9.
Eurasian Opinion, Appln No. 2007/00389/28, Maly Slatoustinsky per., d.10, kv.15, 101000 Moscow, Russia, "EVROMARKPAT", 2007.
Expert Scientific Group on Phase One Clinical Trials, Final Report, Nov. 30, 2006, p. C1, C35-C38.
Ferrand, G., et al., "Synthesis and potential antiallergic activity of new pteridinones and related compounds". Eur. J. Med. Chem, 31, 1996, pp. 273-280. XP—2246920.
Ghandi, L., et al., "An Open-Label Phase II Trial of the PLK Inhibitor BI 2536 in Patients with Sensitive Relapse Small Cell Lung Cancer". ASCO Meeting 2009.
Gil, T. et al., "Final analysis of a phase I single dose-escalation study of the novel polo-like kinase 1 inhibitor BI 6727 in patients with advanced solid tumors." 2010 ASCO Annual Meeting, Journal of Clinical Oncology, Poster Abstract No. 3061.
Giron, G. "Thernal analysis and calorimetric methods in the characterization of plymporphs and solvates". Thermochimica Acta 248, 1995, pp. 1-59.
Goodman & Gilman's the Pharmacological Basis of Therapeutics, Tenth Edition, Chapter 1 "Pharmacokinetics: The Dynamics of Drug Absorption, Distribution, and Elimination." 2001, pp. 3-29.
Goodman and Gilman 9th Edition; 1996; pp. 1225-1232 and 1269-1271.
Goodman-Gilman's "The Pharmacological Basis of Therapeutics". Ninth edition, 1996, pp. 1225-1271.
Gould, P. L., "Salt selection for basic drugs", International Journal of Pharmaceutics, 33(1986), 201-217.
Gura, T. "Cancer Models: Systems for Identifying New Drugs are Often Faulty". Science, Nov. 7, 1997, vol. 278, No. 5340—p. 1041-1042.
International Search Report and Written Opinion for PCT/EP2015/072386 dated Dec. 2, 2015.
Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.
Jamieson, C. et al., "Application of ReactArray Robotics and Design of Experiments Techniques in Optimisation of Supported Reagent Chemistry". Org. Proc. Res. & Dev., 2002, 6, p. 823-825.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kamb, A. "What's wrong with our cancer models?". Nature Reviews Drug Discovery, vol. 4, Feb. 2005, p. 161-165.
Kashima, M. K. et al., "Expression of polo-like kinase (PLK1) in non-Hodgkin's lymphomas". NCBI, PubMed, 2005.
Kimball, S. D. et al., "Cell cycle kinases and checkpoint regulation in cancer". Annual Reports in Medicinal Chemistry, 36, Chapter 14, 2001, pp. 139-148.
Kola, I. et al., "Can the phamaceutical industry reduce attrition rates?" Nature Reviews Drug Discovery, vol. 3, Aug. 2004, p. 711-715.
Krause, M. et al., "Combination of Radiation and Polo-like Kinase 1 Inhibition with BI 6727 in tumour model A431". Strahlenther Onkol, 187, S1, 53 (v17-6), 2011.
Kummer B, et al., "Combination of Radiation and Polo-like Kinase 1 Inhibition with BI6727 in tumour model A431". Vortrag. 20. Symposium „Experimentelle Strahlentherapie und klinische Strahlenbiologie, Exp. Strahlenther. Klin. Strahlenbiol. 20: 93-96 (2011) (Lecture 20, Symposium Experimental Radiation Therapy and Clinical Radiation Biology.).
Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.
Leaf, C. et al., "Why are we losing the war on cancer (and how to win it)". Health Administrator, vol. XVII, No. 1, 2005, p. 172-183.
Leukemia & Lymphoma Society—Disease Information—Lymphoma. www.leukemia-lymphoma.org/all_page?item_id-7030, 2008.
Leukemia & Lymphoma Society—Disease Information. www.leukemia-lymphoma.org/all_page?item_id-7026, 2008.
Holland et al., "Progenitor cells and glioma formation Cur. Open.", Neurology, 2001, 14, pp. 683-688.
Dieter-Hofheinz et al., "An Open-Label, Phase I Study of the Polo-like Kinase-1 Inhibitor, BI 2536, in Patients with Advanced Solid Tumors", Cancer Therapy:Clinical Cancer Res., 2010, 16, pp. 4666-4774.

* cited by examiner

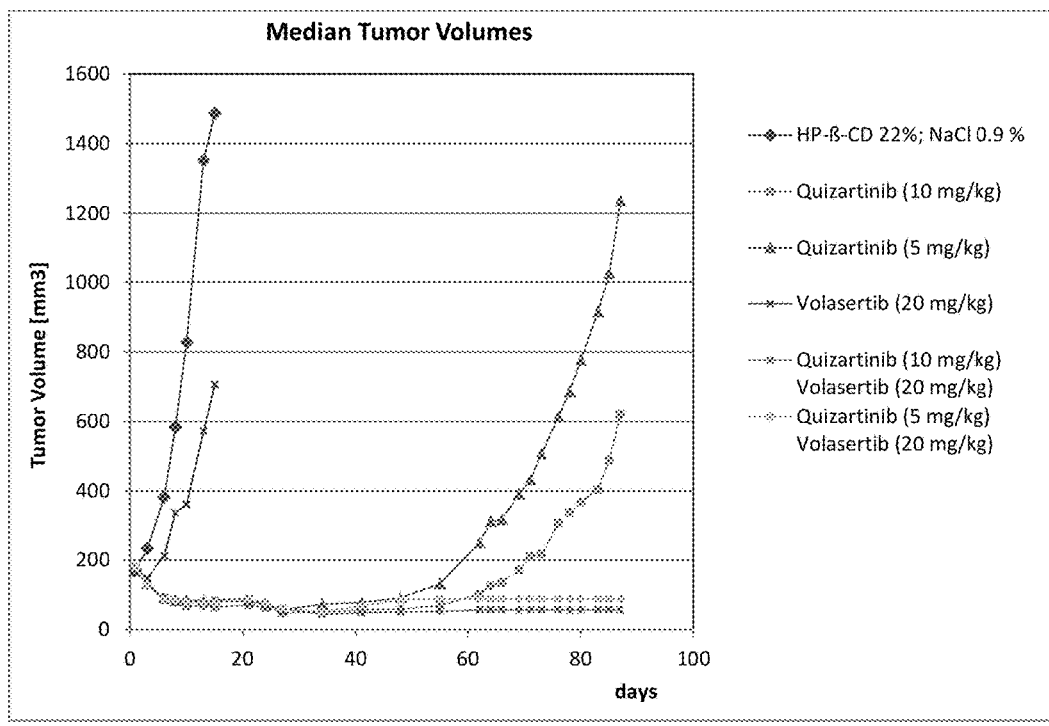

COMBINATION TREATMENT OF ACUTE MYELOID LEUKEMIA AND MYELODYSPLASTIC SYNDROME

RELATED APPLICATIONS

This application claims the benefit of European Application No. EP 14187331.5, filed Oct. 1, 2014, the entire content of which is incorporated herein by reference in its entirety as though fully set forth herein.

FIELD

The present invention relates to the use of Volasertib or a pharmaceutically acceptable salt thereof or the hydrate thereof in combination with Quizartinib or a pharmaceutically acceptable salt thereof or the hydrate thereof for treating patients suffering from acute myeloid leukemia (AML) and myelodysplastic syndrome (MDS).

BACKGROUND OF THE INVENTION

Acute myeloid leukemia (AML), also known as acute myelogenous leukemia, is a cancer of the myeloid line of blood cells, characterized by the rapid growth of abnormal white blood cells that accumulate in the bone marrow and interfere with the production of normal blood cells. As an acute leukemia, AML progresses rapidly and is typically fatal within weeks or months if left untreated. AML is the most prevalent form of adult acute leukemia, particularly among older adults and is slightly more common in men than women. There is an estimated prevalence of 30,000 cases of AML in the US and 47,000 in the EU.

The incidence of AML increases with age with a median age at diagnosis of 67 years. The global incidence CAGR for AML out to 2013 is 1.4%. An aging population, along with an increased incidence of treatment-related AML in cancer survivors, currently accounting for 10-20% of all AML cases, is expected to drive the incidence of AML. In addition, there is some geographic variation in the incidence of AML. In adults, the highest rates are seen in North America, Europe, and Oceania, while adult AML is less frequently diagnosed in Asia and Latin America.

AML accounts for approximately 1.2% of all cancer deaths. The 5 year survival rates for AML are low, driven by therapy failure and patients relapsing. Among patients <65 the 5 year survival rate is 34.4%, among patients >65 it is only 5%.

The WHO classification of myeloid neoplasms and acute leukemia is the current standard for classification of AML and incorporates genetic abnormalities into diagnostic algorithms. This classification is done by examining the appearance of the malignant cells under light microscopy and by using cytogenetics and molecular genetics to characterize any underlying chromosomal abnormalities or genetic changes. The subtypes impact on prognoses, responses to therapy and treatment decisions.

Myelodysplastic syndromes (MDS) are clonal hematopoietic stem-cell disorders characterized by ineffective hematopoiesis, peripheral-blood cytopenias, and increased tendency to progress to acute myeloid leukemia (AML). The age-adjusted incidence of MDS is 3.3 cases per 100,000 people, and this rate appears to be increasing. MDS is primarily a disease of older adults, the median age of patients with MDS is approximately 70 years. This patient population is frequently affected by other comorbid conditions, which often influences treatment decisions. Treatment of MDS is based on prognostic factors that predict survival and progression to AML. Currently, the treatment of patients with MDS is guided by the International Prognostic Scoring System (IPSS). This system stratifies patients into four groups: low, intermediate-1, intermediate-2, and high-risk, based on number of cytopenias, percentage of bone marrow blasts, and karyotype. Low risk and intermediate-1 risk are usually grouped together as lower-risk disease, whereas intermediate-2 risk and high risk are grouped together as higher-risk disease. The survival of patients with higher-risk MDS is significantly different than that of patients with lower-risk disease. Without intervention, median survival of higher-risk patients is close to 12 months. Survival of patients with lower-risk disease is more diverse and ranges from a few months (poor-prognosis, lower-risk disease) to more than a decade. Therefore, the objectives of therapy are different in lower-versus higher-risk disease. While in lower-risk MDS, the goal is to relieve symptoms, manage cytopenias, and minimize the need for transfusions [eg: erythropoiesis-stimulating agents (ESA) and growth factors (GF)], in higher-risk MDS, disease-modifying therapies directed to slowing progression to AML and improving survival are used. These disease modifying therapies include hypomethylating agents (HMA, as e.g. azacitidine), intensive chemotherapy, and allogeneic stem cell transplantation (SCT), with SCT currently being the only known curative modality. Despite these treatment alternatives, the prognosis of patients with higher-risk MDS remains very poor owing to the disappointing activity of standard chemotherapy-based therapies, particularly those with therapy-related MDS, the eventual loss of response to HMA, and the restriction of allogeneic SCT to younger patients with an appropriate donor.

Treatment of higher-risk patients is dependent on whether they are considered to be candidates for intensive therapy (e.g., allogeneic SCT or intensive chemotherapy). Clinical features relevant for this determination include the patient's age, performance status, comorbidities, patient's preference and availability of suitable donor and caregiver. The access to allogeneic SCT is restricted to approximately 8% of patients with MDS, owing to advanced age, concomitant comorbidities and/or donor availability. For higher-risk patients who are not candidates for high-intensity therapy, the use of HMA is considered the standard of care.

The efficacy of chemotherapeutic agents can be improved by using combination therapies with other compounds and/or improving the dosage schedule. Even if the concept of combining several therapeutic agents or improved dosage schedules already has been suggested, there is still a need for new and efficient therapeutic concepts for the treatment of cancer diseases, which show advantages over standard therapies.

Volasertib is a highly potent and selective inhibitor of the serine-threonine Polo like kinase (Plk), a key regulator of cell-cycle progression. Volasertib is a second-generation dihydropteridinone derivative with distinct pharmacokinetic (PK) properties. The problem underlying this invention was to develop a combination treatment and improved dosage schedules for combination therapy of Volasertib and Quizartinib in AML or MDS with maximal activity and limited toxicity.

Volasertib (I) is known as the compound N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide,

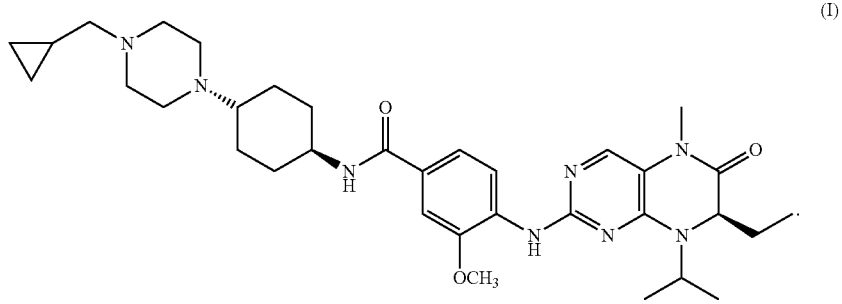

(I)

This compound is disclosed in WO 04/076454. Furthermore, trihydrochloride salt forms and hydrates thereof are known from WO 07/090844. They possess properties which make those forms especially suitable for pharmaceutical use. The above mentioned patent applications further disclose the use of this compound or its monoethanesulfonate salt for the preparation of pharmaceutical compositions intended especially for the treatment of diseases characterized by excessive or abnormal cell proliferation.

Document WO 2006/018182 discloses other combinations for the treatment of diseases involving cell proliferation.

Quizartinib is receptor tyrosine kinase inhibitor with the following chemical structure

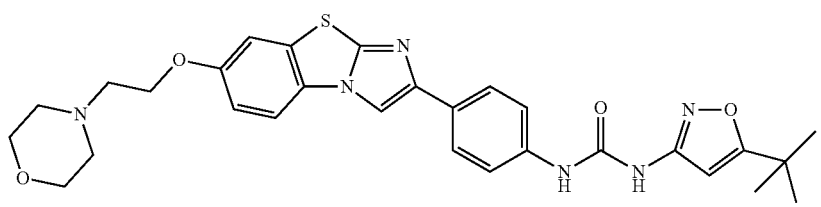 [SMILES: CC(C)(C)c1cc(NC(=O)Nc2ccc(-c3cn4c(n3)sc3cc(OCCN5CCOCC5)ccc34)cc2)no1]

useful for the treatment of AML. This compound inhibits the protooncogene CD135.

SUMMARY OF THE INVENTION

In animal experiments it has been found that the treatment of Hematologic neoplasms with Volasertib and Quizartinib shows a synergistic efficacy profile (e.g. reduced tumor growth compared to either single agent treatment) and good tolerability of the combination treatment regimen.

Accordingly, a first object of the present invention refers to a pharmaceutical combination comprising Volasertib, optionally in the form of a pharmaceutically acceptable salt thereof or a hydrate thereof, and Quizartinib, optionally in the form of a pharmaceutically acceptable salt thereof or a hydrate thereof, for simultaneous, separate or sequential use of the active ingredients.

Another object of the present invention relates to a kit comprising one pharmaceutical composition comprising Volasertib, optionally in the form of a pharmaceutically acceptable salt thereof or a hydrate thereof, and another pharmaceutical composition comprising Quizartinib, optionally in the form of a pharmaceutically acceptable salt thereof or a hydrate thereof.

Another object of the present invention relates to Volasertib, optionally in the form of a pharmaceutically acceptable salt thereof or a hydrate thereof, for use of treating AML or MDS, characterized in that Volasertib is administered in combination with Quizartinib, optionally in the form of a pharmaceutically acceptable salt thereof or a hydrate thereof, wherein both active ingredients can be administered simultaneously, separately or sequentially.

Another object of the present invention relates to Quizartinib, optionally in the form of a pharmaceutically acceptable salt thereof or a hydrate thereof, for use of treating AML or MDS, characterized in that Quizartinib is administered in combination with Volasertib, optionally in the form of a pharmaceutically acceptable salt thereof or a hydrate thereof, wherein both active ingredients can be administered simultaneously, separately or sequentially.

Another object of the present invention relates to Volasertib, optionally in the form of a pharmaceutically acceptable salt thereof or a hydrate thereof, for use of treating AML or MDS characterized in that Volasertib is administered in combination with Quizartinib, optionally in the form of a pharmaceutically acceptable salt thereof or a hydrate thereof, according to a dosage schedule (I) comprising or consisting of
  a) administration of an effective amount of Volasertib or a pharmaceutically acceptable salt thereof or a hydrate thereof on minimally one day, preferably on two days, during a 4 week treatment cycle and
  b) administration of an effective amount of Quizartinib on at least one day during the said 4 week treatment cycle to a patient suffering from AML or MDS.

Another object of the present invention relates to Volasertib, optionally in the form of a pharmaceutically acceptable salt thereof or a hydrate thereof, for use of treating AML or MDS (dosage schedule (II)), characterized in that Volasertib is administered in combination with Quizartinib, optionally in the form of a pharmaceutically acceptable salt thereof or a hydrate thereof, according to dosage schedule (I), wherein Volasertib or a pharmaceutically acceptable salt thereof or a hydrate thereof is administered on day 1 and on one of the days 7, 8, 9, 10, 11, 12, 13, 14, 15, 16, 17, 18, 19, 20 or 21 during a 4 week treatment cycle. Preferably, equal doses of Volasertib are administered on both days of administration.

Another object of the present invention relates to Volasertib, optionally in the form of a pharmaceutically acceptable salt thereof or a hydrate thereof, for use of treating AML or MDS (dosage schedule (III)), characterized in that Volasertib is administered in combination with Quizartinib, optionally in the form of a pharmaceutically acceptable salt thereof or a hydrate thereof, according to one of the above dosage schedules (dosage schedule (I) or (II)) wherein in one embodiment 250 to 500 mg, in another embodiment 250, 300, 350, 400, 450 or 500 mg, yet in another embodiment 300 or 350 mg of Volasertib or a pharmaceutically acceptable salt thereof or a hydrate thereof are administered per day of administration.

Another object of the present invention relates to Volasertib, optionally in the form of a pharmaceutically acceptable salt thereof or a hydrate thereof, for use of treating AML or MDS (dosage schedule (IV)), characterized in that Volasertib is administered in combination with Quizartinib, optionally in the form of a pharmaceutically acceptable salt thereof or a hydrate thereof, according to one of the above dosage schedules (dosage schedule (I), (II) or (III)) wherein Quizartinib is administered on all days during the 4 week treatment cycle.

Another object of the present invention relates to Volasertib, optionally in the form of a pharmaceutically acceptable salt thereof or a hydrate thereof, for use of treating AML or MDS (dosage schedule (V)), characterized in that Volasertib is administered in combination with Quizartinib, optionally in the form of a pharmaceutically acceptable salt thereof or a hydrate thereof, according to one of the above dosage schedules (dosage schedule (I), (II) or (III)) wherein Quizartinib is administered on all days during the 4 week treatment cycle except those days where Volasertib is administered.

Another object of the present invention relates to Volasertib, optionally in the form of a pharmaceutically acceptable salt thereof or a hydrate thereof, for use of treating AML or MDS (dosage schedule (VI)), characterized in that Volasertib is administered in combination with Quizartinib, optionally in the form of a pharmaceutically acceptable salt thereof or a hydrate thereof, according to one of the above dosage schedules (dosage schedule (I), (II) or (III)) wherein Volasertib is administered on day 1 and 15, and Quizartinib is administered on days 2-14 and 16-28 during the 4 week treatment cycle.

Another object of the present invention relates to Volasertib, optionally in the form of a pharmaceutically acceptable salt thereof or a hydrate thereof, for use of treating AML or MDS (dosage schedule (VII)), characterized in that Volasertib is administered in combination with Quizartinib, optionally in the form of a pharmaceutically acceptable salt thereof or a hydrate thereof, according to one of the above dosage schedules (dosage schedule (I), (II) or (III)) wherein Volasertib is administered on day 1 and 15, and Quizartinib is administered on days 3-13 and 17-27 during the 4 week treatment cycle.

Another object of the present invention relates to Volasertib, optionally in the form of a pharmaceutically acceptable salt thereof or a hydrate thereof, for use of treating AML or MDS (dosage schedule (VIII)), characterized in that Volasertib is administered in combination with Quizartinib, optionally in the form of a pharmaceutically acceptable salt thereof or a hydrate thereof, according to one of the above dosage schedules (dosage schedule (I), (II) or (III)) wherein Volasertib is administered on day 1 and 15, and Quizartinib is administered on days 3-13 and 17-27 during the 4 week treatment cycle.

Another object of the present invention relates to Volasertib, optionally in the form of a pharmaceutically acceptable salt thereof or a hydrate thereof, for use of treating AML or MDS (dosage schedule (IX)), characterized in that Volasertib is administered in combination with Quizartinib, optionally in the form of a pharmaceutically acceptable salt thereof or a hydrate thereof, according to one of the above dosage schedules (dosage schedule (I), (II) or (III)) wherein Volasertib is administered on day 1 and 15, and Quizartinib is administered on days 16-28 during the 4 week treatment cycle.

Another object of the present invention relates to Volasertib, optionally in the form of a pharmaceutically acceptable salt thereof or a hydrate thereof, for use of treating AML or MDS (dosage schedule (X)), characterized in that Volasertib is administered in combination with Quizartinib, optionally in the form of a pharmaceutically acceptable salt thereof or a hydrate thereof, according to one of the above dosage schedules (dosage schedule (I), (II), (III), (IV), (V), (VI), (VII), (VIII) or (IX)) wherein in one embodiment 40-200 mg in another embodiment 50 to 150 mg, in another embodiment 60 mg, 90 mg or 135 mg of Quizartinib are administered per day of administration.

Another object of the invention refers to a method of treating AML or MDS characterized in that Volasertib, optionally in the form of a pharmaceutically acceptable salt thereof or a hydrate thereof, and Quizartinib, optionally in the form of a pharmaceutically acceptable salt thereof or a hydrate thereof, are administered according to one of the dosage schedules (I) to (X).

Another object of the invention refers to the use of Volasertib, optionally in the form of a pharmaceutically acceptable salt thereof or a hydrate thereof, for the manufacture of a medicament for treating AML or MDS in patients suffering from AML or MDS wherein the medicament is prepared for administration according to one of the dosage schedules (I) to (X).

Another object of the invention refers to the use of Quizartinib, optionally in the form of a pharmaceutically acceptable salt thereof or a hydrate thereof, for the manufacture of a medicament for treating AML or MDS in patients suffering from AML or MDS wherein the medicament is prepared for administration according to one of the dosage schedules (I) to (X).

Another object of the invention is a pharmaceutical composition comprising an effective amount of Volasertib and an effective amount of Quizartinib, optionally together with an instruction for administration of both active ingredients to a patient suffering from AML or MDS, wherein according to said instruction Volasertib is to be administered according to the above mentioned dosage schedules (I) to (X).

BRIEF DESCRIPTION OF THE FIGURES

FIG. 1 shows the tumor growth kinetics in a nude mouse xenograft model derived from human AML cell line MV4; 11. Tumor-bearing mice were treated for 2 weeks either with vehicle or with 20 mg/kg Volasertib (BI 6727) once a week i.v., 5 mg/kg or 10 mg/kg Quizartinib daily administered p.o. or a combination of Volasertib and Quizartinib. Median tumor volumes are plotted over time. Day 1 was the first day, day 87 the last day of the experiment. Efficacy results from this xenograft models are considered valid for AML as well as MDS.

DETAILED DESCRIPTION OF THE INVENTION

In case Volasertib is administered on minimally two days during a 4 week treatment cycle, then Volasertib is administered on two non-consecutive days during a 4 week treatment cycle.

The administration of an effective amount of Quizartinib on at least one day of the said 4 week treatment cycle means that during the 4 week treatment cycle in which Volasertib is administered minimally one time, also Quizartinib is administered on at least one day.

Preferably, Quizartinib is administered on every day during the 4 week treatment cycle.

The administration of Volasertib on day 1 and 15 during a 4 week treatment cycle means that one dosage of Volasertib or a pharmaceutically acceptable salt or a hydrate thereof is administered on day one and the second dosage is administered on day 15 to the patient suffering from AML or MDS in the four week treatment cycle.

Accordingly, a complete four week treatment cycle according to one of the above mentioned dosage schedules may comprise the following administrations:

Day 1: one dosage of Volasertib (e.g. 300 or 350 mg) and one dosage of Quizartinib (e.g. 40-200 mg);

Day 2 to day 14 (including): one dosage of Quizartinib (e.g. 40-200 mg) per day;

Day 15: one dosage of Volasertib (e.g. 300 or 350 mg) and one dosage of Quizartinib (e.g. 40-200 mg);

Day 16 to day 28 (including): one dosage of Quizartinib (e.g. 40-200 mg) per day.

This treatment cycle can be repeated as long as patients are eligible for repeated cycles, i.e. until relapse, progression of disease and as long as neither patient nor investigator requests treatment discontinuation.

The instruction for coadministration may be in any form suitable for pharmaceuticals, e.g. in form of a leaflet added to the dosage form within secondary packaging or an imprint on the primary or secondary packaging.

Dosages/Volasertib:

For intraveneous treatment Volasertib may be administered to the human patient in a daily dose of 250 to 500 mg/application, preferably 250, 300, 350, 400, 450 or 500 mg/application, more preferably 300 or 350 mg/application. For instance, Volasertib can be administered as a slow intravenous infusion over several hours, e.g. over about 1, 2, 4, 6, 10, 12 or 24 hours, preferably about 1 or 2 hours.

Dosages/Quizartinib:

Quizartinib may be administered in a total daily dose of 40 to 200 mg, e.g. in a total daily dose of 40, 50, 55, 60, 65, 70, 75, 80, 85, 90, 95, 100, 105, 110, 115, 120, 125, 130, 135, 140, 145, 150, 155, 160, 165, 170, 175, 180, 185, 190 or 200 mg one time daily. The total daily dose may also be divided into two or three subdoses to be taken within one day. Preferably, the daily dose is administered in a single dose of 135 mg for male patients and 90 mg for female patients.

However, it may optionally be necessary to deviate from the dosage amounts specified for Volasertib and Quizartinib, depending on the body weight on the method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

Dosage Forms and Formulation Aspects

Regarding any aspects of the invention for Volasertib pharmaceutically acceptable salts or hydrates thereof may be used, preferably trihydrochloride salt forms and hydrates thereof as disclosed in WO 07/090844. Dosages or amounts of the active ingredient provided in the context of this invention refer in any case to the free base equivalent, that is Volasertib in the free base form.

The term "therapeutically effective amount" shall mean that amount of a drug or pharmaceutical agent that will elicit the biological or medical response of a tissue system, animal or human that is being sought by a researcher or clinician, resulting in a beneficial effect for at least a statistically significant fraction of patients, such as an improvement of symptoms, improvement of peripheral blood cell counts, a cure, a reduction in disease load, reduction in tumor mass or leukaemia cell numbers, extension of life, or improvement in quality of life.

Day 1 of a 4 week treatment cycle is defined as that day on which the first dose of Volasertib administered.

Within the present invention the term "AML" is to be understood to encompass all forms of acute myeloid leukemia and related neoplasms according to the 2008 revision of the World Health Organization (WHO) classification of myeloid neoplasms and acute leukemia. These are:

Acute myeloid leukemia with recurrent genetic abnormalities
  AML with t(8;21)(q22;q22); RUNX1-RUNX1T1
  AML with inv(16)(p13.1q22) or t(16;16)(p13.1;q22); CBFB-MYH11
  AML with t(9;11)(p22;q23); MLLT3-MLL
  AML with t(6;9)(p23;q34); DEK-NUP214
  AML with inv(3)(q21 q26.2) or t(3;3)(q21;q26.2); RPN1-EVI1
  AML (megakaryoblastic) with t(1;22)(p13;q13); RBM15-MKL1
  Provisional entity: AML with mutated NPM1
  Provisional entity: AML with mutated CEBPA
Acute myeloid leukemia with myelodysplasia-related changes
Therapy-related myeloid neoplasms
Acute myeloid leukemia, not otherwise specified
  AML with minimal differentiation
  AML without maturation
  AML with maturation
  Acute myelomonocytic leukemia
  Acute monoblastic/monocytic leukemia
  Acute erythroid leukemia
    Pure erythroid leukemia
    Erythroleukemia, erythroid/myeloid
  Acute megakaryoblastic leukemia
  Acute basophilic leukemia
  Acute panmyelosis with myelofibrosis
Myeloid sarcoma
Myeloid proliferations related to Down syndrome
  Transient abnormal myelopoiesis
  Myeloid leukemia associated with Down syndrome
Blastic plasmacytoid dendritic cell neoplasm Within the present invention the term "MDS" is to be understood to encompass all forms of myelodysplastic/myeloproliferative neoplasms (MDS/MPN) and myelodysplastic syndromes according to the 2008 revision of the World Health Organization (WHO) classification of myeloid neoplasms and acute leukemia. These are:

Myelodysplastic/myeloproliferative neoplasms (MDS/MPN)
  Chronic myelomonocytic leukemia
  Atypical chronic myeloid leukemia, BCR-ABL1-negative
  Juvenile myelomonocytic leukemia
  Myelodysplastic/myeloproliferative neoplasm, unclassifiable
  Provisional entity: refractory anemia with ring sideroblasts and thrombocytosis
Myelodysplastic syndrome (MDS)
  Refractory cytopenia with unilineage dysplasia
  Refractory anemia
  Refractory neutropenia
  Refractory thrombocytopenia
  Refractory anemia with ring sideroblasts
  Refractory cytopenia with multilineage dysplasia
  Refractory anemia with excess blasts
  Myelodysplastic syndrome with isolated del(5q)
  Myelodysplastic syndrome, unclassifiable
  Childhood myelodysplastic syndrome
  Provisional entity: refractory cytopenia of childhood In accordance with the present invention Volasertib may be administered by parenteral (e.g. intramuscular, intraperitoneal, intravenous, transdermal or subcutaneous injection), and may be formulated, alone or together, in suitable dosage unit formulations containing conventional non-toxic pharmaceutically acceptable carriers, adjuvants and vehicles appropriate for each route of administration. Dosage forms and formulations of both active ingredients suitable within the present invention are known in the art. For instance, such dosage forms and formulations include those disclosed for Volasertib in WO 2006/018221.

In accordance with the present invention Quizartinib may be administered by oral routes of administration and may be formulated, alone or together, in suitable dosage unit formulations containing conventional non-toxic pharmaceutically acceptable carriers, adjuvants and vehicles appropriate for each route of administration.

The following Examples serve to illustrate the invention without restricting it:

Cells

MV4;11 (CRL-9591) cells were obtained from ATCC. According to the Catalogue of Somatic Mutations in Cancer of the Wellcome Trust Sanger Institute, UK, this cell line carries a mutation in the FLT3 gene. Cells were cultured in T175 tissue culture flasks at 37° C. and 5% CO2. The medium used was IMDM supplemented with 10% fetal calf serum, 1% NEAA, 1% sodium pyruvate and 1% glutamine.

Mice

Mice were 8 week-old athymic female BomTac: NMRI-Foxn1$^{nu}$ purchased from Taconic, Denmark. After arrival in the animal facility, mice were allowed to adjust to ambient conditions for at least 3 days before they were used for experiments. They were housed in Macrolon® type II cages in groups of 5 under standardized conditions at 21.5±1.5° C. temperature and 55±10% humidity. Standardized diet (PROVIMI KLIBA) and autoclaved tap water were provided ad libitum.

Establishment of Tumors, Randomization

To establish subcutaneous tumors, MV4;11 cells were harvested and resuspended in PBS+5% FCS at $5 \times 10^7$ cells/ml. 50 µl of the cell suspension containing $2.5 \times 10^6$ cells was then injected subcutaneously into the right flank of the mice (1 site per mouse). Growth factor reduced BD Matrigel™ Matrix (BD Biosciences) was added to the cell suspension at a ratio of 1:1 before the injection. When tumors were well established and had reached a tumor volume of ~180 mm$^3$, mice were randomly distributed between the treatment and the vehicle control groups 14 days after injecting the cells.

Administration of Test Compounds

Volasertib was dissolved in hydrochloric acid (0.1 N), diluted with 0.9% NaCl and injected intravenously into the tail vein. An administration volume of 10 ml per kg body weight was used. The solution was freshly made up each injection day. Quizartinib was dissolved in 22% HP-β-CD and administered p.o. An administration volume of 10 ml per kg body weight was used.

The application solution was prepared for one week of treatment and kept at 4° C.

Monitoring Tumor Growth and Side Effects

The tumor diameter was measured three times a week with a caliper. The volume of each tumor [in mm$^3$] was calculated according to the formula "tumor volume=length*diameter$^2$*π/6". To monitor side effects of treatment, mice were inspected daily for abnormalities and body weight was determined three times a week. Control animals and animals of the single agent Volasertib treatment arm were sacrificed when the control tumors reached a size of approximately 1400 mm$^3$ on average. Animals of the Quizartinib single agent and combination treatment arms were sacrificed when the tumors reached a size of approximately 1400 mm$^3$ or at the end of the study.

Example 1

Nude Mouse Xenograft Model Derived from Human AML Cell Line MV4;11

Results of an experiment comparing treatment of xenografts in mice with Volasertib alone (20 mg/kg), administered once weekly, Quizartinib alone (5 or 10 mg/kg), administered daily, and the combination of Volasertib (20 mg/kg once a week)/Quizartinib (5 or 10 mg/kg administered daily) are shown in FIG. 1. Animals were treated for 14 days followed by an observation period without treatment up to day 87. FIG. 1 shows the outgrowth of the tumor from the treatment groups with single agent quizartinib, but maintained tumor control until the end of the study in the combination arms. Further, a beneficial side effect profile was demonstrated as body weight gain in the combination group was comparable to single-agent Quizartinib.

The invention claimed is:
1. A method of treating a patient suffering from myeloid leukemia (AML) and/or myelodysplastic syndrome (MDS), comprising: administering to the patient Volasertib or a pharmaceutically acceptable salt thereof or a hydrate thereof, and Quizartinib or a pharmaceutically acceptable salt thereof or a hydrate thereof, wherein the Volasertib or a pharmaceutically acceptable salt thereof or a hydrate thereof and Quizartinib or a pharmaceutically acceptable salt thereof or a hydrate thereof are administered simultaneously, separately or sequentially.

2. The method of claim 1, wherein Volasertib or a pharmaceutically acceptable salt thereof or a hydrate thereof, and Quizartinib or a pharmaceutically acceptable salt thereof or a hydrate thereof, are administered according to a dosage schedule (I), comprising:
  a) administration of a therapeutically effective amount of Volasertib or a pharmaceutically acceptable salt thereof or a hydrate thereof on minimally one day during a 4 week treatment cycle and
  b) administration of a therapeutically effective amount of Quizartinib or a pharmaceutically acceptable salt thereof or a hydrate thereof on at least one day of the said 4 week treatment cycle,
to the patient.

3. The method of claim 1, wherein Volasertib or a pharmaceutically acceptable salt thereof or a hydrate thereof and Quizartinib or a pharmaceutically acceptable salt thereof or a hydrate thereof are administered according to a dosage schedule (I), comprising:
   a) administration of a therapeutically effective amount of Volasertib or a pharmaceutically acceptable salt thereof or a hydrate thereof on minimally two days during a 4 week treatment cycle and
   b) administration of a therapeutically effective amount of Quizartinib or a pharmaceutically acceptable salt thereof or a hydrate thereof on at least one day of the said 4 week treatment cycle,
to the patient.

4. The method of claim 1, wherein 250 to 500 mg of Volasertib or a pharmaceutically acceptable salt thereof or a hydrate thereof is administered per day of administration.

5. The method of claim 1, wherein 40 to 200 mg of Quizartinib or a pharmaceutically acceptable salt thereof or a hydrate thereof is administered per day of administration.

6. The method of claim 1, wherein Quizartinib or a pharmaceutically acceptable salt thereof or a hydrate thereof is administered on all days during the 4 week treatment cycle.

7. The method of claim 2, wherein Volasertib or a pharmaceutically acceptable salt thereof or a hydrate thereof is administered on day 1 and 15, and Quizartinib or a pharmaceutically acceptable salt thereof or a hydrate thereof is administered on days 2-14 and 16-28 during the 4 week treatment cycle.

8. The method of claim 2, wherein Volasertib or a pharmaceutically acceptable salt thereof or a hydrate thereof is administered on day 1 and 15, and Quizartinib or a pharmaceutically acceptable salt thereof or a hydrate thereof is administered on days 3-13 and 17-27 during the 4 week treatment cycle.

9. The method of claim 2, wherein Volasertib or a pharmaceutically acceptable salt thereof or a hydrate thereof is administered on day 1 and 15, and Quizartinib or a pharmaceutically acceptable salt thereof or a hydrate thereof is administered on days 16-28 during the 4 week treatment cycle.

10. The method of claim 3, wherein Volasertib or a pharmaceutically acceptable salt thereof or a hydrate thereof is administered on day 1 and 15, and Quizartinib or a pharmaceutically acceptable salt thereof or a hydrate thereof is administered on days 2-14 and 16-28 during the 4 week treatment cycle.

11. The method of claim 3, wherein Volasertib or a pharmaceutically acceptable salt thereof or a hydrate thereof is administered on day 1 and 15, and Quizartinib or a pharmaceutically acceptable salt thereof or a hydrate thereof is administered on days 3-13 and 17-27 during the 4 week treatment cycle.

12. The method of claim 3, wherein Volasertib or a pharmaceutically acceptable salt thereof or a hydrate thereof is administered on day 1 and 15, and Quizartinib or a pharmaceutically acceptable salt thereof or a hydrate thereof is administered on days 16-28 during the 4 week treatment cycle.

13. A pharmaceutical composition comprising an effective amount of Volasertib or a pharmaceutically acceptable salt thereof or a hydrate thereof, and an effective amount of Quizartinib or a pharmaceutically acceptable salt thereof or a hydrate thereof.

14. The pharmaceutical composition according to claim 13 for treating AML and/or MDS.

15. A pharmaceutical combination comprising Volasertibor a pharmaceutically acceptable salt thereof or a hydrate thereof, and Quizartinib or a pharmaceutically acceptable salt thereof or a hydrate thereof, for simultaneous, separate or sequential administration to and treatment of a patient suffering from AML and/or MDS.

* * * * *